United States Patent
Ohtake et al.

(10) Patent No.: US 7,488,940 B2
(45) Date of Patent: Feb. 10, 2009

(54) REFLECTION TYPE TERAHERTZ SPECTROMETER AND SPECTROMETRIC METHOD

(75) Inventors: Hideyuki Ohtake, Kariya (JP); Makoto Yoshida, Nagoya (JP); Koichiro Tanaka, Souraku-gun (JP); Masaya Nagai, Kyoto (JP)

(73) Assignee: Aisin Seiki Kabushiki Kaisha, Kariya-shi (JP)

( * ) Notice: Subject to any disclaimer, the term of this patent is extended or adjusted under 35 U.S.C. 154(b) by 311 days.

(21) Appl. No.: 10/558,300

(22) PCT Filed: May 24, 2004

(86) PCT No.: PCT/JP2004/007423

§ 371 (c)(1),
(2), (4) Date: Nov. 28, 2005

(87) PCT Pub. No.: WO2004/106900

PCT Pub. Date: Dec. 9, 2004

(65) Prior Publication Data

US 2006/0231762 A1    Oct. 19, 2006

(30) Foreign Application Priority Data

May 29, 2003    (JP)    ............................. 2003-153160

(51) Int. Cl.
*G01N 21/31*    (2006.01)
(52) U.S. Cl. .................................................. 250/341.3
(58) Field of Classification Search .............. 250/341.1, 250/340, 341.3
See application file for complete search history.

(56) References Cited

U.S. PATENT DOCUMENTS 4,129,781 A * 12/1978 Doyle ...................... 250/341.3

(Continued)

FOREIGN PATENT DOCUMENTS

EP    1 079 225 A1    2/2001

(Continued)

OTHER PUBLICATIONS

G. Torosyan, et al., "Application of Narrowband Tunabel $TH_z$-Radiation for Biomedical Sensing", Proceedings of the Second Joint EMBS/MES Conference, vol. 3, Oct. 2002, pp. 2335-2336.

(Continued)

*Primary Examiner*—David P Porta
*Assistant Examiner*—David S Baker
(74) *Attorney, Agent, or Firm*—Oblon, Spivak, McClelland, Maier & Neustadt, P.C.

(57) ABSTRACT

A reflection-type terahertz spectrometer includes an input optical path through which terahertz waves are propagated, an irradiating mechanism that irradiates a sample with terahertz waves propagated through the input optical path, an output optical path through which terahertz waves exiting from the irradiating mechanism are propagated, and a detector that receives and detects the terahertz waves propagated through the output optical path. The irradiating mechanism has at least one planar interface and a refractive index greater than that of a peripheral region contacting the planar interface and is disposed between the input optical path and the output optical path such that the terahertz waves propagated through the input optical path to be incident on the planar interface undergo total internal reflection at the planar interface, and the sample is disposed in the peripheral region contacting the planar interface of the irradiating mechanism. When the terahertz waves undergo the total internal reflection at the planar interface, the sample is irradiated with evanescent waves scattering from the planar interface to the peripheral region contacting the planar interface, so as to measure a spectrum.

18 Claims, 4 Drawing Sheets

U.S. PATENT DOCUMENTS

| | | | | |
|---|---|---|---|---|
| 5,532,488 | A | * | 7/1996 | Ishibashi et al. ......... 250/341.3 |
| 5,534,698 | A | * | 7/1996 | Ohshima et al. ....... 250/339.11 |
| 5,578,828 | A | * | 11/1996 | Brown et al. ................ 250/342 |
| 5,789,750 | A | * | 8/1998 | Nuss ....................... 250/338.1 |
| 5,894,127 | A | * | 4/1999 | Dando et al. ............. 250/341.3 |
| 6,301,041 | B1 | * | 10/2001 | Yamada ...................... 359/333 |
| 7,145,148 | B2 | * | 12/2006 | Alfano et al. ............ 250/341.8 |
| 7,214,940 | B2 | * | 5/2007 | Cluff et al. ............... 250/341.1 |
| 2004/0065832 | A1 | * | 4/2004 | Cluff et al. ............... 250/341.1 |
| 2005/0179905 | A1 | | 8/2005 | Ohtake et al. |

FOREIGN PATENT DOCUMENTS

| | | | | |
|---|---|---|---|---|
| GB | 2371111 | A | * | 7/2002 |
| GB | 2384555 | A | * | 7/2003 |
| GB | 2396695 | A | * | 6/2004 |
| JP | 05-072119 | | | 3/1993 |
| JP | 7-103890 | | | 4/1995 |
| JP | 08-201272 | | | 8/1996 |
| JP | 9-68495 | | | 3/1997 |
| JP | 9-292339 | | | 11/1997 |
| JP | 2000-146836 | | | 5/2000 |
| JP | 2000146836 | A | * | 5/2000 |
| JP | 2003-14620 | | | 1/2003 |
| WO | WO 02/057750 | A2 | * | 7/2002 |
| WO | WO02/057750 | A2 | * | 7/2002 |

OTHER PUBLICATIONS

Koichiro Tanaka, "Jikan Ryoiki Tera Hertz Zenhansha Gensui Bunkoho", Oyo Butsurigaku Kankei Rengo Koenkai Koen Yokoshu, vol. 51st, No. 0, Mar. 2004, p. 31.

Koichiro Tanaka, "Jikan Ryoiki Tera Hertz Zenhansha Gensui Bunko Sochi no Kochiku to sono Hyoka", Extended Abstract; the Japan Society of Applied Physics, vol. 64th, No. 3, 2003, p. 1000.

Ryo Karasawa et al., "Kinsetsujo o Mochiita Tera Hertz Imaging System", Oyo Butsurigaku Kankei Rengo Koenkai Koen Yokoshu, vol. 49th, No. 3, Mar. 2002, p. 1102.

Kiyomi Sakai et al., "Terahertz Time Domain Spectroscopy and Imaging", Laser Review, vol. 30, No. 7, Jul. 2002, pp. 376-384.

Offermann, V. et al., "Experimental aspects of attenuated total reflectance spectroscopy in the infrared", Vibrational Spectroscopy, vol. 8, pp. 135-140, 1995.

Tetsuhiko Ohba, et al., "Far-Infrared Optical Constants of Liquid Acetonitrile as Measured by a Laser Attenuated Total Reflection Method", Chemical Physics Letters, XP-002411518, vol. 117, No. 5, Jun. 28, 1985, pp. 397-399.

D. E. Brown, et al., "A high-resolution Fourier transform spectrometer for far infrared magneto-optic spectroscopy of magnetic materials", Infrared Physics & Technology, XP-002411519, vol. 40, No. 3, 1999, pp. 219-230.

A. Hartstein, et al., "Investigation of optic-phonon-magnetoplasmon-type surface polaritons on $n$-InSb", Physical Review B, XP-002411520, vol. 12, No. 8, Oct. 15, 1975, pp. 3186-3199.

Neil Everall, et al., "Characterisation of biaxial orientation gradients in poly(ethylene terephthalate) films and bottles using polarised attenuated total reflection FTIR spectroscopy", Polymer, XP-004354970, vol. 43, No. 15, 2002, pp. 4217-4223.

Lynn L. Deibler, et al., "Infrared Polarimetry Using Attenuated Total Reflection", Proceedings of the SPIE, XP 008001654, vol. 3754, Jul. 1999, pp. 99-107.

S. Ikawa, et al., "Measurement of Far-Infrared Optical Constants By ATR High Rep Rate High Performance Plasma Focus as a Powerful Radiationsource", International Journal of Infrared and Millimeter Waves, vol. 6, No. 4, XP-001248762, 1985, pp. 287-306.

A. R. El-Gohary, et al., "Observation of surface phonon-polaritons on a MQW specimen by attenuated-total-reflection spectroscopy", Semiconductor Science and Technology, vol. 4, No. 5, XP-020031980, May 1, 1989, pp. 388-392.

T. Dumelow, et al., "Far-IR Spectroscopy of Bulk and Surface Phonon-Polaritons on Epitaxial Layers of CdTe Deposited by Plasma MOCVD on GaAs Substrates", Materials Science and Engineering, vol. B5, No. 2, XP-002422081, Jan. 1990, pp. 217-221.

N. Raj, et al., "Theory of far-infrared attenuated total reflection from semiconductor superlattices", Journal of Physics C: Solid State Physics, vol. 20, No. 31, XP-020010485, Nov. 10, 1987, pp. 5203-5216.

A. Hatta, et al., "Electronic absorption enhancement for TCNQ films on silver by excitation of surface plasmon polaritons", Applied Surface Science, vol. 51, No. 3/4, XP-000863744, 1991, pp. 193-200.

A. Hatta, et al., "Polarization-Modulation Electronic Absortion Study of Copper Phthalocyanine Films on Silver by Surface Plasmon Resonance Spectroscopy", Applied Surface Science, vol. 40, No. 1-2, XP-002422082, Nov. 1989, pp. 9-18.

E. Hutter, et al., "Fourier Transform Infrared Spectroscopy Using Polarization Modulation and Polarization Selective Techniques for Internal and External Reflection Geometries: Investigation of Self-Assembled Octadecylmercaptan on a Thin Gold Film", J. Phys. Chem., vol. 107, No. 31, XP-002422083, Apr. 7, 2003, pp. 7812-7819.

Erik Goormaghtigh, et al., "Attenuated total reflection infrared spectroscopy of proteins and lipids in biological membranes", Biochimica et Biophysica Acta, vol. 1422, No. 2, XP-004281745, Jul. 6, 1999, pp. 105-185.

Petra Heinrich, et al., "Determination of Organic Compounds By IR/ATR Spectroscopy with Polymer-Coated Internal Reflection Elements", Applied Spectroscopy, vol. 44, No. 10, XP-000169320, Dec. 1, 1990, pp. 1641-1646.

P. Y. Han, et al., "A direct comparison between terahertz time-domain spectroscopy and far-infrared fourier transform spectroscopy", Journal of Applied Physics, vol. 89, No. 4, XP-012052979, Feb. 15, 2001, pp. 2357-2359.

\* cited by examiner

REFLECTION TYPE TERAHERTZ SPECTROMETER AND SPECTROMETRIC METHOD

TECHNICAL FIELD

The present invention relates to an instrument and a method which measures a spectrum of a sample under analysis in a terahertz frequency range.

BACKGROUND ART

Terahertz waves are electromagnetic waves with frequencies between 0.1 and 10 THz (wavelengths between 30 μm and 3000 μm). This wavelength range approximately corresponds to the infrared to far infrared region. Terahertz spectrometers using these terahertz waves have been developed.

The terahertz spectrometers are divided into a transmission type which irradiates terahertz waves on a sample and detects transmitted light, and a reflection type which irradiates terahertz waves on a sample and detects reflected light. The transmission-type spectrometers need samples to be in the form of a thin film of about 1 μm, since terahertz waves, which fall in the infrared to far infrared region, are strongly absorbed by most substances. Therefore, much attention has been paid to the reflection-type spectrometers which do not limit the thickness of samples.

As shown in FIG. 7, a conventional reflection-type spectrometer generates terahertz waves by pumping InAs 30 by an ultrashort pulse laser, irradiates the terahertz waves on a sample 35 by way of off-axis parabolic mirrors 31, 34, and makes reflected light incident on a photoconductive dipole antenna 37 by off-axis parabolic mirrors 34, 36 for photoelectric detection (See Kiyomi SAKAI et al, "Terahertz Time Domain Spectroscopy and Imaging", The Review of Laser Engineering, Vol. 30, No. 7, July 2002, pp. 376-384). In this conventional reflection-type spectrometer, first light reflected by the sample 35 is photoelectrically detected and next, light reflected by a metallic mirror which is placed in the same position as the sample 35 is also photoelectrically detected for reference. Then complex amplitudes in the frequency domain obtained by computing the Fourier transform of the respective detected photoelectric waveforms are compared with each other so as to derive reflectivity and phase shift. The most important problem of this spectrometer is that an error occurs in phase shift unless measurement is conducted with the metallic mirror and the sample placed in exactly the same position. Besides, its samples are limited to solids. And liquid, amorphous living organisms or the like cannot be measured.

As mentioned above, the conventional reflection-type terahertz spectrometer requires the sample and the metallic mirror to be placed in the same position and has made large measurement errors. To decrease the measurement errors, these two objects need to be placed in the same position with high accuracy. This placement takes a lot of time and this spectrometer is poor in practicality. In addition, since its samples are limited to solids, this spectrometer is poor in general versatility.

The present invention has been made in view of the above problems of the conventional reflection-type terahertz spectrometer. It is an object of the present invention to provide a reflection-type terahertz spectrometer and spectrometric method in which a metallic mirror does not have to be placed in the same position as a sample and samples are not limited to solids.

DISCLOSURE OF THE INVENTION

The reflection-type terahertz spectrometer of the present invention comprises an input optical path through which terahertz waves are propagated, an irradiating means which irradiates a sample with the terahertz waves propagated through the input optical path, an output optical path through which terahertz waves having exiting from the irradiating means are propagated, and a detecting means which receives and detects the terahertz waves propagated through the output optical path, and is characterized in that the irradiating means has at least one planar interface and a refractive index greater than that of a peripheral region contacting the planar interface and is disposed between the input optical path and the output optical path such that the terahertz waves propagated through the input optical path to be incident on the planar interface undergo total internal reflection at the planar interface, and the sample is disposed in the peripheral region contacting the planar interface of the irradiating means, and when the terahertz waves undergo the total internal reflection at the planar interface, the sample is irradiated with evanescent waves scattering from the planar interface to the peripheral region contacting the planar interface, so as to measure a spectrum.

The evanescent waves scattering from the planar interface of the irradiating means play interaction with the sample and the terahertz waves including information of the evanescent waves have exited from the irradiating means to the output optical path. In the absence of a sample in the neighborhood of the planar interface, terahertz waves including information of evanescent waves which do not play interaction with the sample have exited, so these terahertz waves in the absence of a sample can be used for reference. There is no need to conduct reference measurement by placing a metallic mirror. In addition, owing to the use of the interaction between the evanescent waves scattering from the planar interface of the irradiating means and the sample, samples are not limited to solids.

This terahertz spectrometer can further comprise a polarization control means which controls polarization of the terahertz waves in the midst of the input optical path, so as to control polarization of the evanescent waves.

By employing this means, the interaction between longitudinal waves or transverse waves and the sample can be selectively played and it becomes possible to observe absorption spectrum by plasma, longitudinal phonons in a semiconductor, etc. First, when the terahertz waves are p-polarized by the polarization control means and are made incident on the irradiating means, the evanescent waves scattering from the planar interface are subjected to longitudinal wave modulation, thereby having both a longitudinal wave component and a transverse wave component. Second, when the terahertz waves are s-polarized by the polarization control means and are made incident on the irradiating means, evanescent waves having a transverse wave component alone are obtained. The longitudinal wave component can be extracted by differentiating these two waves.

The irradiating means can be formed of one of silicon, germanium, diamond, III-V semiconductors including GaAs, II-VI semiconductors including ZnSe, silica glass, fluororesin, polyethylene, and polycarbonate-containing organic materials.

By thus forming the irradiating means, terahertz wave absorption loss inside the irradiating means can be decreased.

The reflection-type terahertz spectrometer can further comprise a housing with an opening for accommodating the input optical path and the output optical path, and the irradiating means may be disposed so as to close the opening with the planar interface of the irradiating means.

Due to their long wavelengths, terahertz waves are strongly absorbed by atmospheric $H_2O$, etc., which becomes noise in terahertz spectrometry. However, the inner space of the housing can be purged with nitrogen, etc. or vacuumed, and as a result absorption by $H_2O$, etc. can be prevented.

A thin film which has a refractive index smaller than that of the irradiating means and does not absorb terahertz waves can be formed on the planar interface of the irradiating means.

Owing to this arrangement, terahertz waves can be totally internally reflected at the planar interface of the irradiating means which is in contact with the thin film, and at the same time evanescent waves can scatter from the planar interface to the thin film. Therefore, as long as the thin film has a sufficiently small thickness, terahertz spectrometry can be performed even when a sample having a refractive index larger than that of the irradiating means is disposed on this thin film.

A reflection-type terahertz spectrometric method of the present invention for dissolving the above mentioned problems, which measures a spectrum of a sample in a terahertz wavelength region by irradiating terahertz waves on the sample and detecting reflected waves from the sample by a detecting means, is characterized by placing, in the midst of an optical path between the generating means and the detecting means, an optical medium having a refractive index larger than that of the optical path such that terahertz waves incident on the optical medium undergo total internal reflection at an interface of the optical medium so as to generate evanescent waves from the interface, and by placing the sample in the neighborhood of the interface of the optical medium so as to irradiate the evanescent waves on the sample and measure a spectrum.

In the above method, polarization of the evanescent waves can be controlled by polarizing the terahertz waves from the generating means to be incident on the optical medium by a polarization control means.

Moreover, when polarization of the evanescent waves is controlled as above, the reflection-type terahertz spectrometric method of the present invention can measure a spectrum by p-polarizing the terahertz waves from the generating means to be incident on the optical medium by the polarization control means, next measure a spectrum by s-polarizing the terahertz waves from the generating means to be incident on the optical medium by the polarization control means, and differentiate these two spectra.

The optical medium used in the terahertz spectrometric method of the present invention can be formed of one of silicon, germanium, diamond, III-V semiconductors including GaAs, II-VI semiconductors including ZnSe, silica glass, fluororesin, polyethylene, polycarbonate-containing organic materials.

Moreover, in the method of the present invention, the optical path and the sample can be spatially isolated from each other at the interface of the optical medium.

Furthermore, in the method of the present invention, the optical medium can be provided, at the interface, with a thin film which has a refractive index smaller than that of the optical medium and does not absorb the terahertz waves such that the terahertz waves undergo total internal reflection at the interface on which the thin film is formed.

When the reflection-type terahertz spectrometer of the present invention is used in carrying out the aforementioned reflection-type terahertz spectrometric method of the present invention, the irradiating means can be used as the optical medium.

BEST MODE FOR CARRYING OUT THE INVENTION

Figure 1:
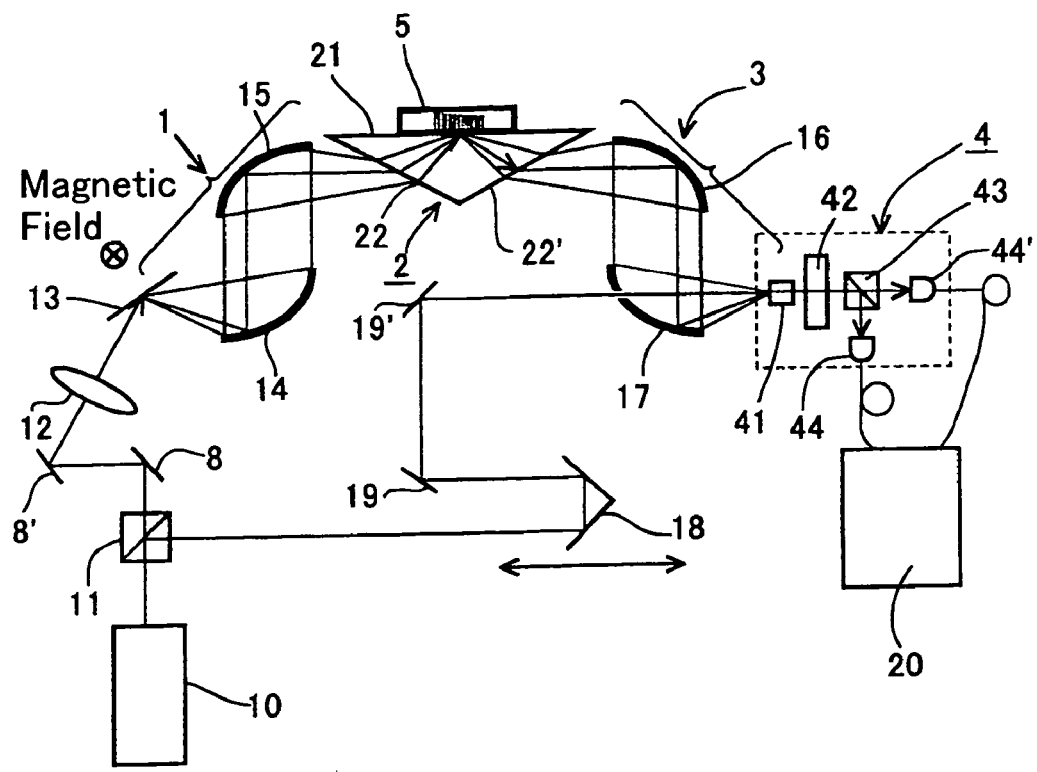
FIG. 1 is a schematic diagram showing the structure of a reflection-type terahertz spectrometer according to a first preferred embodiment.

Terahertz waves can be generated by irradiating a photoconductive semiconductor switch (i.e., a low-temperature-grown GaAs (LT-GaAs) having a metallic antenna thereon), a surface of a bulk semiconductor such as InAs, a semiconductor quantum well, a nonlinear optical crystal, a high-temperature superconductor, etc. with ultrashort light pulses having a duration of not more than 100 fs from a mode-locked titanium sapphire laser or the like and providing pumping. Generally, ultrashort light pulses are focally irradiated in order to increase the efficiency and intensity of terahertz waves generating. The photoconductive switch has a high efficiency of generating terahertz waves, but is destructed when irradiated with a strong laser for an increase in the efficiency of generating terahertz waves, and degrades with the passage of time. InAs shows the highest efficiency of generating terahertz waves among bulk semiconductors, and exhibits an increase in the efficiency and intensity of terahertz waves generating especially upon the application of a strong magnetic field. It is to be noted that terahertz waves can also be generated by irradiating a LT-GaAs photoconductive switch with two cw single-mode semiconductor lasers or cw multi-mode semiconductor lasers having similar emission wavelengths. This has a merit of not requiring an expensive femtosecond laser.

The input optical path through which terahertz waves generated by the terahertz wave generating means are propagated is a terahertz wave passage from the terahertz wave generating means to the subsequent irradiating means, and can be open space or a space closed by a body tube, etc. A closed space is preferable because absorption by $H_2O$, etc. can be prevented, for instance, by purging the inner space with nitrogen. In measuring a small sample, a condenser optical system is preferably provided in the midst of the input optical path. This enables measurement of small samples. The reason why the condenser optical system is required is as follows: Terahertz waves are generated, as mentioned above, by focally irradiating InAs, etc. with ultrashort optical pulses, so the terahertz waves generated from the terahertz wave generating means are generally spherical waves. Therefore, it is preferable to collimate these terahertz waves once by an off-axis parabolic mirror or the like and focus the collimated terahertz waves by another off-axis parabolic mirror or the like so as to make the terahertz waves incident on the irradiating means.

Then the intensity of the terahertz waves can be increased and spectrum detection sensitivity can be enhanced. Moreover, when a polarization control means which controls polarization of the terahertz waves is additionally provided in the midst of the input optical path, the polarization control means can be a sheet polarizer, which is formed by drawing fluororesin, polyethylene, polycarbonate-containing organic materials, etc. in one direction, a wire grid polarizer, and so on.

The irradiating means has only to have at least one planar interface and a refractive index larger than that of a peripheral region contacting the planar interface. The irradiating means can be in the shape of a half-cut cylinder, a hemisphere, a triangular prism, etc. The material of the irradiating means is preferably silicon, germanium, diamond, III-V semiconductors including GaAs and II-VI semiconductors including ZnSe, silica glass such as fused silica and crystal quarts, fluororesin, polyethylene, or polycarbonate-containing organic materials. This is because terahertz wave absorption loss inside the irradiating means can be small. The III-V and II-VI semiconductors have a small terahertz wave absorption loss inside themselves but have a strong reflection at the interface because of their large refractive indices, so the III-V and II-VI semiconductors may have an antireflection film, etc. on the plane of incidence and the plane of exit, if necessary. The use of silica glass, polyethylene, etc. enables a change in soft materials under visible light irradiation and pump-probe spectroscopy, which is a type of time-resolved spectroscopy, owing to their transparency even to the visible light (i.e., small absorption loss). As the fluororesin, it is particularly preferable to employ polytetrafluoroethylene. The use of polytetrafluoroethylene enables spectra of samples including acid or alkali to be measured, since polytetrafluoroethylene is especially resistant to acid or alkali. Besides, if the planar interface of the irradiating means is put upward, a spectra can be measured simply by placing a sample on the planar interface. Therefore, powdery chemicals and organic functional materials such as DNA in liquid can be used as samples. Moreover, bulk superconductors, which cannot be measured by conventional reflection-type spectrometers because of their large refractive indices, can be used as samples. If polarization of the evanescent waves is controlled by controlling polarization of the terahertz waves incident on the irradiating means, even influence of Josephson plasma (longitudinal waves), which is associated with superconductivity phenomena of high-temperature superconductors, is detectable and high-temperature superconductors can also be used as samples.

The irradiating means can be formed of the abovementioned materials and a thin film having a refractive index smaller than that of the irradiating means can be formed on its planar interface. When the irradiating means is formed of silica, the thin film can be formed of polyethylene, for instance. This thin film needs to have such a small thickness that evanescent waves can reach a sample placed on the thin film. This can be achieved by the film thickness of about 1 μm.

A sample under analysis is disposed in a peripheral region contacting the planar interface of the irradiating means. The peripheral region is a region where evanescent waves from the planar interface scatter and is of the order of terahertz wavelength, namely, in the range of 3 μm to 300 μm from the planar interface.

The output optical path through which terahertz waves having exiting from the irradiating means are propagated is a terahertz wave passage from the irradiating means to the subsequent detecting means, and can be open space or a space closed by a body tube, etc. A closed space is preferable because absorption by $H_2O$, etc. can be prevented, for instance, by purging the inner space with nitrogen. A condenser optical system is desirably provided in the midst of the output optical path. It is preferable to collimate the terahertz waves which have undergone total internal reflection at the planar interface of the irradiating means once by an off-axis parabolic mirror or the like and focus the collimated terahertz waves by another off-axis parabolic mirror or the like so as to make the terahertz waves incident on the detecting means. Then the intensity of the terahertz waves can be increased and spectrum detectivity can be enhanced.

The detecting means can be a bolometer and a device using electro-optic (EO) effects such as a photoconductive antenna and ZnTe. The bolometer can convert terahertz waves into electric signals single-handedly but is poor in responsibility. The device using electro-optic effect serves to irradiate EO crystal with terahertz waves to be detected and detect a variation in refractive index induced by the electric field of the terahertz waves by means of a variation in the polarization of the probe light traveling through the EO crystal. This method using the EO effects has a merit of being capable of measuring time waveform, namely, phase information, which cannot be measured by the bolometer. The variation in the polarization of the probe light can be detected by a polarization control element and a photoelectric detection element. For example, detection can be carried out by converting the probe light transmitted through the EO crystal into linearly polarized light by a ¼ wave plate, splitting that linearly polarized light by a polarization beam splitter, detecting the split lights by two photodiodes, etc., and inputting two electric signals into a balance detector.

The housing with an opening for accommodating the input optical path and the output optical path has only to be sealed when the opening is closed. Its material is not limited, but, if the inner space needs to be vacuumed, stainless steel is desirable. This is because no gas generation occurs. When a laser light source irradiating the terahertz wave generating means is disposed outside the housing, the housing has to be provided with a laser introducing window for irradiating the generating means with a laser from the laser light source.

First Preferred Embodiment

FIG. 1 is a schematic view showing the structure of a reflection-type terahertz spectrometer according to a preferred embodiment of the present invention.

The spectrometer of this preferred embodiment comprises an input optical path 1 through which terahertz waves from a terahertz wave generating means 13 are propagated, an irradiating means 2 which irradiates a sample 5 with the terahertz waves propagated through the input optical path 1, an output optical path through which terahertz waves having exiting from the irradiating means 2 are propagated, and a detecting means 4 which receives and detects the terahertz waves propagated through the output optical path 3.

The terahertz wave generating means 13 is a bulk semiconductor InAs in which ultrashort light pulses with a wavelength of 800 nm, a pulse width of 100 fs, a repetition of 80 MHz from a femtosecond laser light source 10 are split in half by a polarization beam splitter 11, bent by bend mirrors 8, 8' and then focally irradiated by a lens 12. As shown in FIG. 1, the InAs 13 is applied with a magnetic field of 1 tesla by a magnet (not shown) in a direction perpendicular to the plane of incidence (the plane of the page). Though the terahertz wave generating means 13 is a part of the spectrometer of this preferred embodiment, the terahertz wave generating means 13 can be provided independently from the spectrometer.

On the input optical path 1, there are inserted an off-axis parabolic mirror 14 for collimation and an off-axis parabolic mirror 15 for focused radiation. The off-axis parabolic mirrors 14, 15 have a focal length of 200 mm.

Figure 2:
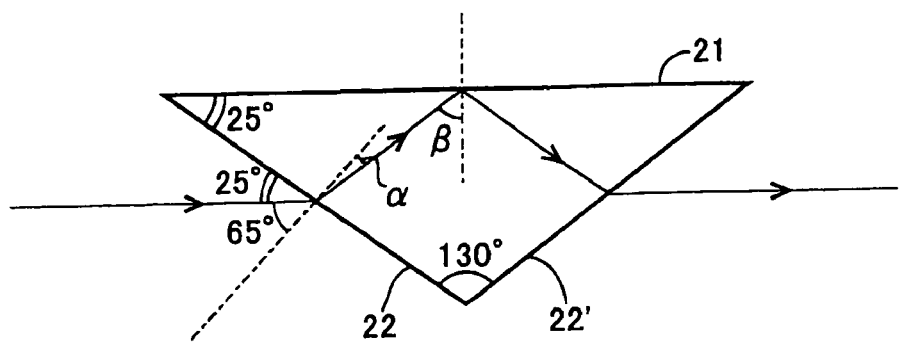
FIG. 2 is a partial view of FIG. 1, showing that total reflection occurs at a planar interface in the reflection-type terahertz spectrometer of the first preferred embodiment.

The irradiating means 2 is an isosceles prism with a vertex angle of 130° formed of polytetrafluoroethylene (refractive index n=1.45). The side opposite to the vertex becomes a planar interface 21 and the prism 2 is disposed in the air (refractive index $n_0$=1.0) between the input optical path 1 and the output optical path 3 such that the terahertz waves are incident from one side 22 of the isosceles sides and exit from the other side 22'. As shown in FIG. 2, the terahertz waves incident on the side 22 in a parallel direction to the planar interface 21 have an incident angle of 65° to the side 22. The refraction angle α is:

$$\alpha=\sin^{-1}[(1/1.45)\sin 65°]=38.7°.$$

The incident angle β to the planar interface 21 is:

$$\beta=63.7°.$$

The critical angle θc, at which total reflection occurs, is:

$$\theta c=\sin^{-1}(1/1.45)=43.6°$$

Since the incident angle β is greater than the critical angle θc, total reflection occurs. The terahertz waves totally reflected travel in symmetry with the incident waves from the total reflection point and exit from the side 22', since the irradiating means 2 is an isosceles prism.

On the output optical path 3, there are inserted an off-axis parabolic mirror 16 for collimation and an off-axis parabolic mirror 17 for focused radiation. The off-axis parabolic mirrors 16, 17 have a focal length of 200 mm. The paraboloidal mirror 17 has a hole through which a half of the ultrashort light pulses split by the polarization beam splitter 11 pass.

The detecting means 4 comprises EO crystal ZnTe 41, a ¼ wave plate 42, a polarization beam splitter 43 and photodiodes 44, 44'. The terahertz waves propagating through the output optical path 3 is focally irradiated on the ZnTe 41 by way of the off-axis parabolic mirror 17. In the absence of terahertz waves, the ZnTe 41 does not have a variation in refractive index, so linearly polarized ultrashort light pulses incident through the hole of the off-axis parabolic mirror 17 become circularly polarized light after passing through the ¼ wave plate 42. Hence, the p-polarized light component and the s-polarized light component are identical with each other, so electric signals output from the photodiodes 44, 44' after split by the polarization beam splitter 43 have the same value, and the balance (a difference between the two electric signals) measured by a balance detector 20 becomes zero. In the presence of terahertz waves, the refractive index of the ZnTe 41 is varied by the terahertz wave electric field, so polarization of the linearly polarized ultrashort light pulses incident through the hole of the off-axis parabolic mirror 17 is rotated and they become elliptically-polarized light after passing through the ¼ wave plate 42. Hence, there is a difference between the p-polarized light component and the s-polarized light component. Electric signals output from the photodiodes 44, 44' after split by the polarization beam splitter 43 have different values and a balance is detected. This balance is proportional to the strength of the electric field of the terahertz waves incident on the ZnTe. In order to match, on the ZnTe 41, the timing of the terahertz waves irradiated focally by the off-axis parabolic mirror 17 and that of the ultrashort light pulses incident through the hole of the off-axis parabolic mirror 17, the ultrashort light pulses separated by the polarization beam splitter 11 are subjected to delay control by a delay line which comprises a cat's-eye mirror 18 and bend mirrors 19, 19'.

Figure 3:
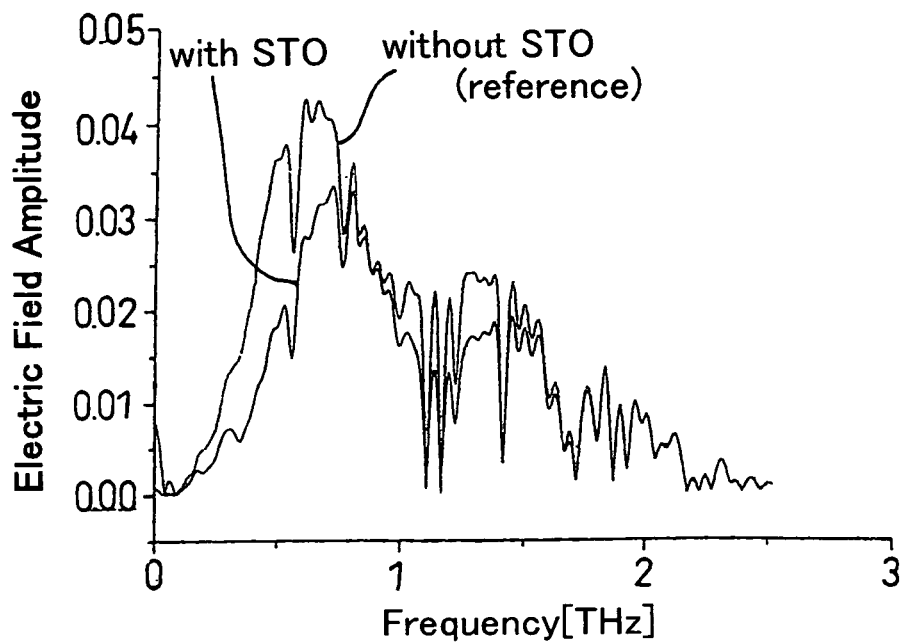
FIG. 3 shows the spectra of radiation (in the presence and absence of a sample) measured by the reflection-type terahertz spectrometer of the first preferred embodiment.
Figure 4:
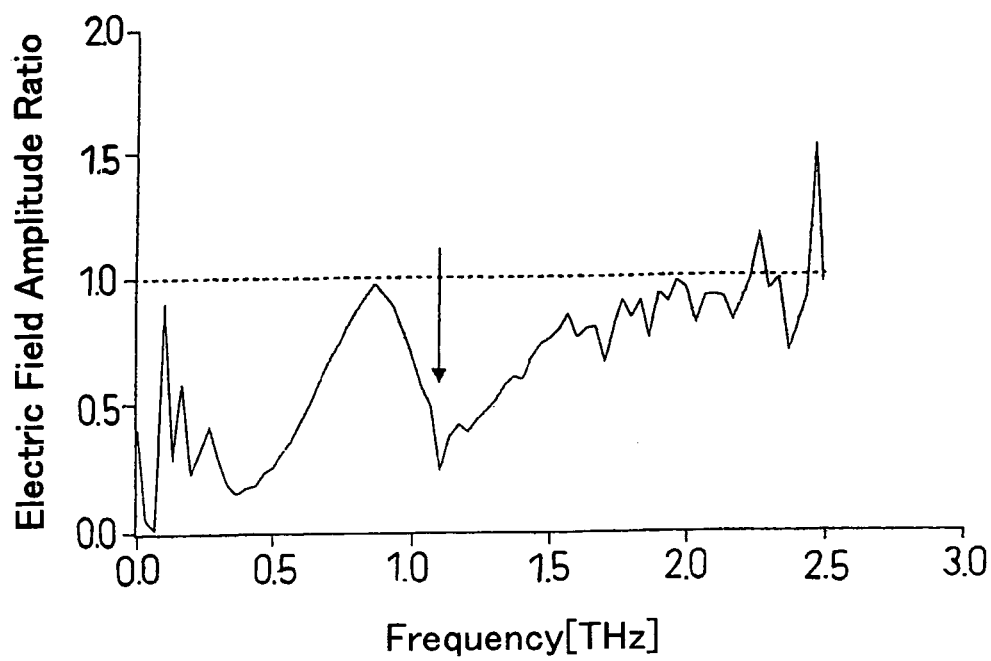
FIG. 4 shows a spectrum obtained by dividing the spectrum of the radiation in the presence of the sample with the spectrum of the radiation in the absence of the sample.

Measurement was conducted by using dielectric strontium titanate (STO) as a sample 5 and pressing the STO 5 against the planar interface 21 of the prism 2, and the results are shown in FIGS. 3 and 4. FIG. 3 shows the Fourier transform of the time variation of the terahertz wave electric field detected by the balance detector 20 in the presence and absence (for reference) of the STO 5 at the planar interface 21. The spectra of the two are identical in a high frequency region but largely different from each other in a low frequency region. It is to be noted that most of the absorption lines are due to absorption by atmospheric $H_2O$. FIG. 4 shows the result of dividing the spectrum of the STO by the reference spectrum. In FIG. 4, the absorption lines due to $H_2O$ disappear and absorption is apparent around 1.1 THz as indicated by the arrow.

Second Preferred Embodiment

Figure 5:
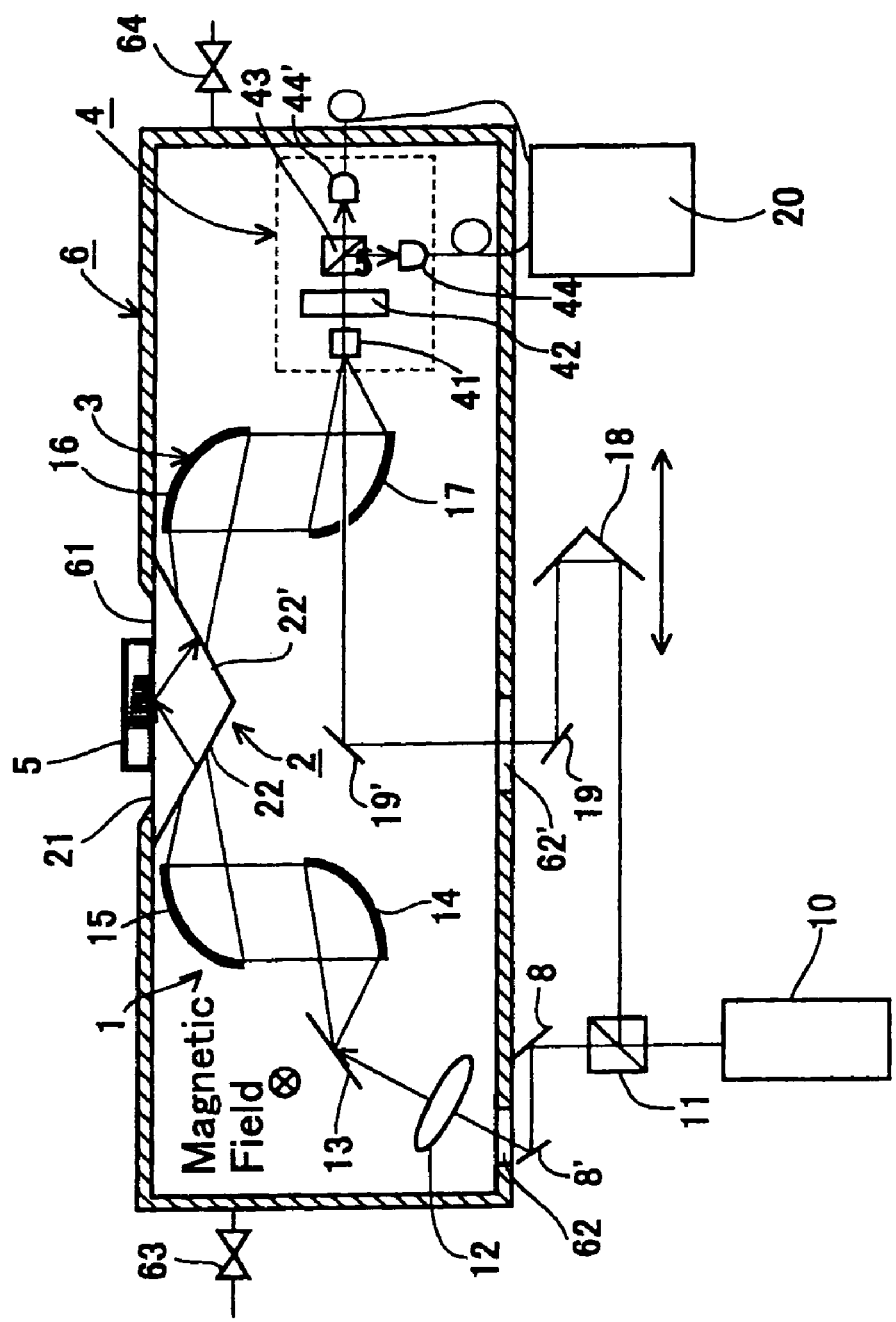
FIG. 5 is a schematic diagram showing the structure of a reflection-type terahertz spectrometer according to a second preferred embodiment.

FIG. 5 is a schematic diagram showing the structure of the reflection-type terahertz spectrometer according to a second embodiment of the present invention. Although the spectrometer of the first preferred embodiment was affected by absorption by atmospheric $H_2O$, the spectrometer of the second preferred embodiment is constructed so as not to be affected by absorption by $H_2O$. Hence, the spectrometer of the second preferred embodiment comprises a housing 6 which isolates the input optical path 1, the irradiating means 2 and the output optical path 3 of the first preferred embodiment (shown in FIG. 1) from the outside. In FIG. 5, the same constitutional elements as those of the first preferred embodiment are denoted by the same reference numerals as those of FIG. 1 and repetition of description is omitted.

The housing 6 comprises an opening 61, windows 62, 62', a gas inlet valve 63 and a gas exhaust valve 64, and the opening 61 is sealed with the planar interface 21 of the irradiating means 2. The inner space of the housing 6 was purged with nitrogen by connecting a nitrogen gas cylinder to the side of the inlet valve 63 and opening the exhaust valve 64, and measurement was conducted by using the same STO as used in the first preferred embodiment as a sample 5. As a result, no absorption by $H_2O$ was observed and the signal-to-noise ratio was greatly improved.

Third Preferred Embodiment

Figure 6:
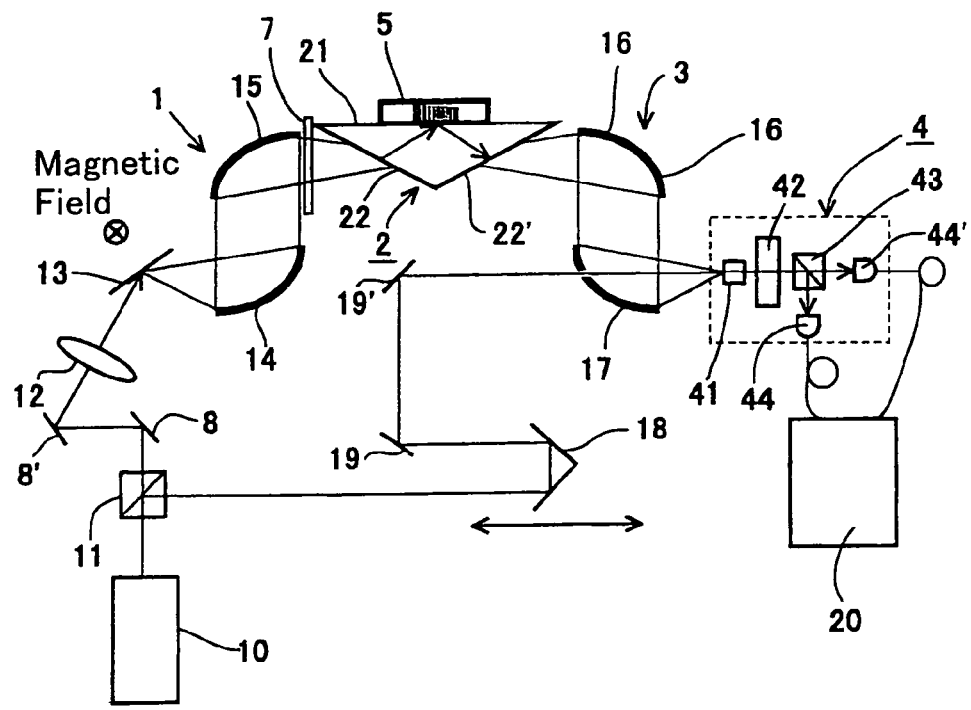
FIG. 6 is a schematic diagram showing the structure of a reflection-type terahertz spectrometer according to a third preferred embodiment.
Figure 7:
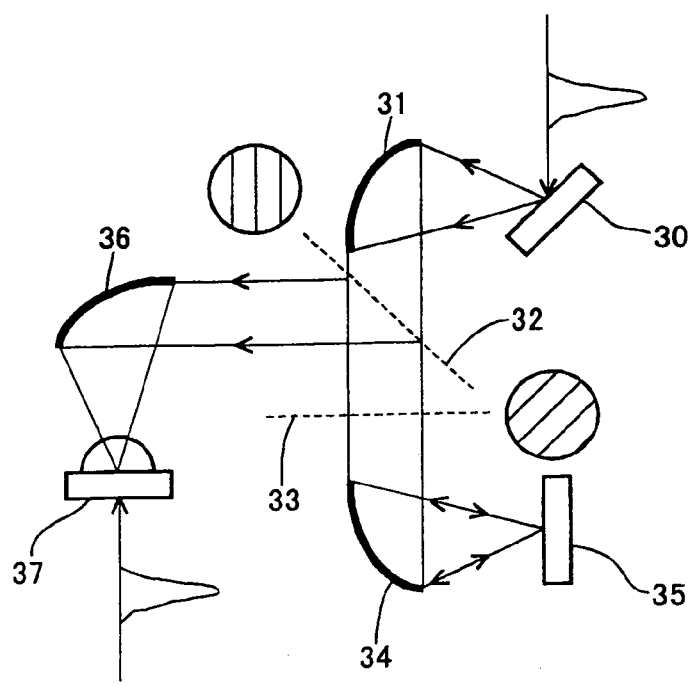
FIG. 7 is a schematic diagram showing the structure of a conventional reflection-type terahertz spectrometer.

FIG. 6 is a schematic diagram showing the structure of a reflection-type terahertz spectrometer according to a third preferred embodiment of the present invention. The spectrometer of this preferred embodiment is constructed so as to be capable of observing an absorption spectrum by plasma, longitudinal phonons in a semiconductor, etc. Hence, the spectrometer of this preferred embodiment comprises a polarizer 7, which is a polarization control means, on the input optical path 1 of the first preferred embodiment (shown in FIG. 1). In FIG. 6, the same constitutional elements as those of the first preferred embodiment are denoted by the same reference numerals as those of FIG. 1 and repetition of description is omitted.

A compound semiconductor GaAs was used as a sample 5. First the terahertz waves which were p-polarized by controlling the polarizer 7 were made incident on the side 22 of the prism 2 and a spectrum was measured. Next, the terahertz waves which were s-polarized by turning the polarizer 7 at an angle of 90° were made incident on the side 22 and a spectrum was measured. Then a spectrum of a difference between the spectrum of the p-polarized light and the spectrum of the s-polarized light was calculated, and as a result, absorption was confirmed around 7 THz. This corresponds with ν=7.2 THz, which was calculated from the separately calculated phonon's energy E=h ν=0.03 eV, where h is Planck's constant, ν is phonon frequency.

INDUSTRIAL APPLICABILITY

As mentioned above, the reflection-type terahertz spectrometer and spectrometric method of the present invention is useful in measuring a spectrum in the frequency range from 0.1 to 10 THz (in the wavelength region from 30 μm to 3000 μm) by means of reflection, and suitable for measuring absorption spectra of semiconductors and superconductors, etc.

The invention claimed is:

1. A reflection-type terahertz spectrometer, comprising:
   an input optical path through which terahertz waves are propagated,
   an irradiating means which irradiates a sample with said terahertz waves propagated through said input optical path,
   an output optical path through which terahertz waves having been exiting from said irradiating means are propagated,
   a detecting means which receives and detects said terahertz waves propagated through said output optical path, and
   a polarization control means which controls polarization of said terahertz waves at said input optical path,
   wherein said irradiating means has at least one planar interface and a refractive index greater than that of a peripheral region contacting said planar interface and is disposed between said input optical path and said output optical path such that said terahertz waves propagated through said input optical path to be incident on said planar interface undergo total internal reflection at said planar interface, and
   said sample is disposed in said peripheral region contacting said planar interface of said irradiating means, and when said terahertz waves undergo said total internal reflection at said planar interface, said sample is irradiated with evanescent waves scattering from said planar interface to said peripheral region contacting said planar interface, so as to measure a spectrum.

2. The reflection-type terahertz spectrometer according to claim 1, wherein said irradiating means is formed of one of silicon, germanium, diamond, III-V semiconductors including GaAs and II-VI semiconductors including ZnSe, silica glass, fluororesin, polyethylene, or polycarbonate-containing organic materials.

3. The reflection-type terahertz spectrometer according to claim 1, further comprising a housing with an opening for accommodating said input optical path and said output optical path, said irradiating means being disposed so as to close said opening with said planar interface.

4. The reflection-type terahertz spectrometer according to claim 1, wherein a thin film which has a refractive index smaller than that of said irradiating means and does not absorb said terahertz waves is formed on said planar interface of said irradiating means.

5. A reflection-type terahertz spectrometric method, comprising:
   measuring a spectrum of a sample in a terahertz wavelength region by irradiating terahertz waves from a terahertz wave generating means on said sample and detecting reflected waves from said sample by a detecting means,
   placing, within an optical path between said generating means and said detecting means, an optical medium having a refractive index larger than that of said optical path such that terahertz waves incident on said optical medium undergo total internal reflection at an interface of said optical medium so as to generate evanescent waves from said interface,
   controlling, using a polarization control means, polarization of said evanescent waves by polarizing said terahertz waves from said generating means to be incident on said optical medium,
   placing said sample in a vicinity of said interface of said optical medium so as to irradiate said evanescent waves on said sample and measure a spectrum.

6. The reflection-type terahertz spectrometric method according to claim 5, wherein the measuring measures a spectrum by p-polarizing said terahertz waves from said wave generating means to be incident on said optical medium by said polarization control means, and next measures a spectrum by s-polarizing said terahertz waves from said wave generating means to be incident on said optical medium by said polarization control means and differentiating these two spectra.

7. The reflection-type terahertz spectrometric method according to claim 5, wherein said optical medium is formed of one of silicon, germanium, diamond, III-V semiconductors including GaAs and II-VI semiconductors including ZnSe, silica glass, fluororesin, polyethylene, or polycarbonate-containing organic materials.

8. The reflection-type terahertz spectrometric method according to claim 5, wherein said optical path and said sample are spatially isolated from each other at said interface of said optical medium.

9. The reflection-type terahertz spectrometric method according to claim 5, wherein said optical medium is provided, at said interface, with a thin film which has a refractive index smaller than that of said optical medium and does not absorb said terahertz waves such that said terahertz waves undergo total internal reflection at said interface on which said thin film is formed.

10. A reflection-type terahertz spectrometer, comprising:
   an input optical path through which polarized terahertz waves are propagated,
   an irradiating means which irradiates a sample with said polarized terahertz waves propagated through said input optical path,
   an output optical path through which polarized terahertz waves having been exiting from said irradiating means are propagated, and
   a detecting means which receives and detects said polarized terahertz waves propagated through said output optical path, wherein:
   said irradiating means has at least one planar interface and a refractive index greater than that of a peripheral region contacting said planar interface and is disposed between said input optical path and said output optical path such that said polarized terahertz waves propagated through said input optical path to be incident on said planar interface undergo total internal reflection at said planar interface,
   said sample is disposed in said peripheral region contacting said planar interface of said irradiating means, and when said polarized terahertz waves undergo said total internal reflection at said planar interface, said sample is irradiated with evanescent waves scattering from said planar interface to said peripheral region contacting said planar interface, so as to measure a spectrum, and the reflection-type terahertz spectrometer further comprising a polarization control means which controls polarization of said polarized terahertz waves at said input optical path, so as to control polarization of said evanescent waves.

11. The reflection-type terahertz spectrometer according to claim 10, wherein said irradiating means is formed of one of silicon, germanium, diamond, III-V semiconductors including GaAs and II-VI semiconductors including ZnSe, silica glass, fluororesin, polyethylene, or polycarbonate-containing organic materials.

12. The reflection-type terahertz spectrometer according to claim 10, further comprising a housing with an opening for accommodating said input optical path and said output optical path, said irradiating means being disposed so as to close said opening with said planar interface.

13. The reflection-type terahertz spectrometer according to claim 10, wherein a thin film which has a refractive index smaller than that of said irradiating means and does not absorb said polarized terahertz waves is formed on said planar interface of said irradiating means.

14. A reflection-type terahertz spectrometer, comprising:
a terahertz wave generating means for generating terahertz waves,
an input optical path through which terahertz waves propagate,
a polarization control means polarizing the terahertz waves,
an irradiating means which irradiates a sample with the polarized terahertz waves propagated through said input optical path,
an output optical path through which terahertz waves having been exiting from said irradiating means are propagated, and
a detecting means which receives and detects said terahertz waves propagated through said output optical path,
wherein said irradiating means has at least one planar interface and a refractive index greater than that of a peripheral region contacting said planar interface and is disposed between said input optical path and said output optical path such that said terahertz waves propagated through said input optical path to be incident on said planar interface undergo total internal reflection at said planar interface, and said sample is disposed in said peripheral region contacting said planar interface of said irradiating means, and when said terahertz waves undergo said total internal reflection at said planar interface, said sample is irradiated with evanescent waves scattering from said planar interface to said peripheral region contacting said planar interface, so as to measure a spectrum.

15. The reflection-type terahertz spectrometer according to claim 14, wherein said irradiating means is formed of one of silicon, germanium, diamond, III-V semiconductors including GaAs and II-VI semiconductors including ZnSe, silica glass, fluororesin, polyethylene, or polycarbonate-containing organic materials.

16. The reflection-type terahertz spectrometer according to claim 14, further comprising a housing with an opening for accommodating said input optical path and said output optical path, said irradiating means being disposed so as to close said opening with said planar interface.

17. The reflection-type terahertz spectrometer according to claim 14, wherein a thin film which has a refractive index smaller than that of said irradiating means and does not absorb said terahertz waves is formed on said planar interface of said irradiating means.

18. A reflection-type terahertz spectrometer, comprising:
a device measuring a spectrum of a sample in a terahertz wavelength region by irradiating terahertz waves from a terahertz wave generating means on said sample and detecting reflected waves from said sample by a detecting means,
an optical path placed between said generating means and said detecting means,
an optical medium having a refractive index larger than that of said optical path such that terahertz waves incident on said optical medium undergo total internal reflection at an interface of said optical medium so as to generate evanescent waves from said interface, and
a polarization control device polarizing said terahertz waves from said generating means to be incident on said optical medium,
wherein said sample being placed in a vicinity of said interface of said optical medium so as to irradiate said evanescent waves on said sample and measure a spectrum.

* * * * *